(12) United States Patent
Brown et al.

(10) Patent No.: US 9,775,769 B2
(45) Date of Patent: Oct. 3, 2017

(54) ELECTRONIC MASSAGING ORTHOTIC COMPRESSION GLOVE

(71) Applicant: BROWNMED, INC, Spirit Lake, IA (US)

(72) Inventors: Ivan E. Brown, Spirit Lake, IA (US); Teryle L. Kounkel, Spirit Lake, IA (US); Brandon Rodriguez, Spirit Lake, IA (US); Gregory A. Grubb, Dixon, IL (US)

(73) Assignee: Brownmed, Inc., Boston, MA (US)

( * ) Notice: Subject to any disclaimer, the term of this patent is extended or adjusted under 35 U.S.C. 154(b) by 604 days.

(21) Appl. No.: 13/948,264

(22) Filed: Jul. 23, 2013

(65) Prior Publication Data

US 2015/0032036 A1    Jan. 29, 2015

(51) Int. Cl.
| | | |
|---|---|---|
| *A61H 11/00* | (2006.01) | |
| *A61H 23/02* | (2006.01) | |
| *A61F 13/10* | (2006.01) | |
| *A61H 1/00* | (2006.01) | |

(52) U.S. Cl.
CPC ........... *A61H 23/02* (2013.01); *A61F 13/104* (2013.01); *A61H 1/008* (2013.01); *A61H 2201/165* (2013.01); *A61H 2201/1635* (2013.01); *A61H 2205/065* (2013.01)

(58) Field of Classification Search
CPC ...... A61H 1/00; A61H 1/0285; A61H 1/0288; A61H 7/00; A61H 7/004; A61H 7/007; A61H 2007/009; A61H 23/00; A61H 23/02; A61H 23/0254; A61H 23/0263; A61H 2201/00; A61H 21/0153; A61H 2201/0157; A61H 2201/12; A61H 2201/1207; A61H 2205/00; A61H 2205/065; A61H 2205/067; A61H 1/008; A61H 2201/1635; A61H 2201/165; A61F 13/104

See application file for complete search history.

(56) References Cited

U.S. PATENT DOCUMENTS

| | | | |
|---|---|---|---|
| 2,286,089 | A | 6/1942 | Harris |
| 2,350,817 | A | 6/1944 | Purves et al. |
| 2,918,055 | A | 12/1959 | Boerger |
| 3,623,481 | A | 11/1971 | Curran |
| 4,116,233 | A | 9/1978 | Scaduto |
| 5,070,862 | A | 12/1991 | Berlant |
| 5,519,292 | A | 5/1996 | Taylor et al. |
| 5,601,529 | A | 2/1997 | Wollman |
| 5,768,709 | A | 6/1998 | Newkirk et al. |
| 6,203,509 | B1 | 3/2001 | Duboff |
| 6,401,252 | B1 | 6/2002 | Dean |
| 6,646,855 | B2 | 11/2003 | Buening et al. |
| 6,748,604 | B2 | 6/2004 | Duboff et al. |
| 7,707,654 | B1 | 5/2010 | Spence |
| 2002/0083508 | A1 | 7/2002 | Dean |
| 2003/0221238 | A1 | 12/2003 | Duboff et al. |
| 2004/0087881 | A1 | 5/2004 | Gross |
| 2005/0143679 | A1 | 6/2005 | Gelber et al. |
| 2008/0216207 | A1 | 9/2008 | Tsai |
| 2013/0018289 | A1* | 1/2013 | Nussbaum ............ A61H 23/02 601/46 |

(Continued)

*Primary Examiner* — Steven Douglas
(74) *Attorney, Agent, or Firm* — McKee, Voorhees & Sease, PLC

(57) ABSTRACT

An electronic vibrating compression glove which simultaneously provides compression and vibration therapy to arthritic hands.

12 Claims, 5 Drawing Sheets

(56) References Cited

U.S. PATENT DOCUMENTS

2013/0090581 A1* 4/2013 Yamazaki .......... A41D 19/0024
601/81
2014/0066925 A1* 3/2014 Howard ................ A61H 23/00
606/38

* cited by examiner

ELECTRONIC MASSAGING ORTHOTIC COMPRESSION GLOVE

FIELD OF THE INVENTION

This invention relates to an electronic massaging orthotic compression glove which simultaneous applies compression and vibrating massage to a wearer's hand.

BACKGROUND OF THE INVENTION

This invention relates to an improved electronic vibrating compression glove. The glove is operable by a power source and simultaneously compresses and vibrates the wearer's hand. It is useful for massage therapy for injured and/or arthritic hands. There are available massaging devices that attach to individual fingers or are handheld but they all differ from the present invention in important ways. Some examples of existing massaging devices are described below.

U.S. Pat. No. 5,070,862 shows a flexible glove that uses a source of pulse energy such as a TENS unit to provide electrical nerve stimulation. Publication 2004/0087881 provides electrical and heat vibrating with a full leather glove. Publication 2003/0221238 provides a loose fitting glove with a large motor source attached to its exterior. Publication 2002/0083508 is a vibrating glove with a plurality of balls being movably disposed near the ends of the fingers. Publication 2005/0143679 shows a glove of conventional configuration with a heating element and vibratory massage. Publication 2008/0216207 shows a glove with a vibrational device to ease finger pain and a glove palm surface with grip dots. U.S. Pat. No. 6,646,855 shows a stun glove to give an electrical shock to an assailant. U.S. Pat. No. 6,401,252 shows a massaging glove with vibratory balls. U.S. Pat. No. 6,748,604 shows a massage glove again with conventional glove material and a bulky separate rechargeable battery. U.S. Pat. No. 7,707,654 shows a massage glove and bead packet. U.S. Pat. No. 6,203,509 is directed to a finger massage device that is mountable to a user's finger. U.S. Pat. Nos. 5,601,529 and 5,519,292 are both directed to massage apparatuses that are mountable on the hand and wrist of the user. U.S. Pat. No. 4,116,233 is directed to a large fixed massage ball, and is mountable to all of the fingers of one hand. U.S. Pat. No. 3,623,481 is directed to a gum massage implement that is mounted to the posterior side of a finger of the user, and a method of finger massaging gums. U.S. Pat. Nos. 2,918,055 and 2,350,817 are both directed to hand massagers. Both of the devices depicted in these patents are secured to the posterior side of several fingers of the user. These devices also impart vibratory forces to the hand of the user, which is in turn used for massaging either the user or another. U.S. Pat. No. 2,286,089 is directed to a hand attachment means for a vibrator. The reference from the French Ministry of Industry and Commerce (Ministere de L'Industrie et du Commerce), number 59.368, describes a massage glove) utilizes hot air to heat the glove, and the massaging vibrations imparted by the glove are caused by a piston mechanism pushing pulsations of hot air through the glove.

While all of the above described gloves are relevant to the present invention in the sense that they show gloves which operably massage in one way or another, they are all distinguishable on several grounds and they all have deficiencies which do not allow them to achieve the results of the present invention. None collectively show in a single glove, compression, vibration transferred to the top of digit joints and a glove that appears normal.

Accordingly it is a primary objective of the present invention to provide a compression glove that is vibrational at the top of the digit joints that can have a normal appearance and that allows the hands to still perform normal tasks while they are worn.

Another objective is to provide a glove that provides some relief to people with chronic hand problems, often from arthritic joints of the digits.

A yet further objective is to provide a glove that is comfortable and avoids significant migration of its electrical components.

And still further it is an objective of the present invention to provide a glove that helps maintain the feel of the massage longer, even after the electrical components are shut off.

Another objective is to provide a silicone cover on the fabric encasing the battery housing to minimize migration.

The method and manner of accomplishing each of the above objectives, as well as other benefits will be apparent from the detailed description which follows.

SUMMARY OF THE INVENTION

This invention is an electronic massaging glove which simultaneously provides orthotic compression and vibrational therapy, which is distinct from nerve stimulating electrical therapy. Moreover, such is achieved with a glove which has the appearance of an ordinary dress glove, if one so wishes. It's accomplished by using stretchable fabric material for the glove and an overlay of the same stretchable fabric material that covers the battery, on/off switch, electrical connecting wires and vibrating motors. The motors are placed on the top side of the digits to expressly enhance vibration at locations where there is less fibrous or fatty tissue to absorb vibration (tops of the digits). With respect to the thumb, it is preferred to have the motor at the base of the thumb (CMC joint). The gloves may include other optional features as described below.

DETAILED DESCRIPTION OF THE PREFERRED EMBODIMENTS

The invention is shown generally in FIGS. 1-6 as may be seen in the figures. The glove 10 is stretchable having upper 12, lower surface 14, and its fingers and thumb 16, 18, 20, 22, and 24 made of a stretchable fabric material. The stretchable fabric material acts to provide orthotic compression important to the co-acting simultaneous compression and electronic massaging action of the present glove.

A suitable compression material that is stretchable is available and can be purchased. Preferably it is 90% cotton and about 10% Spandex® and most preferably 92% cotton and about 8% Spandex®. The material can be purchased from a variety of commercial sources.

Figure 1:
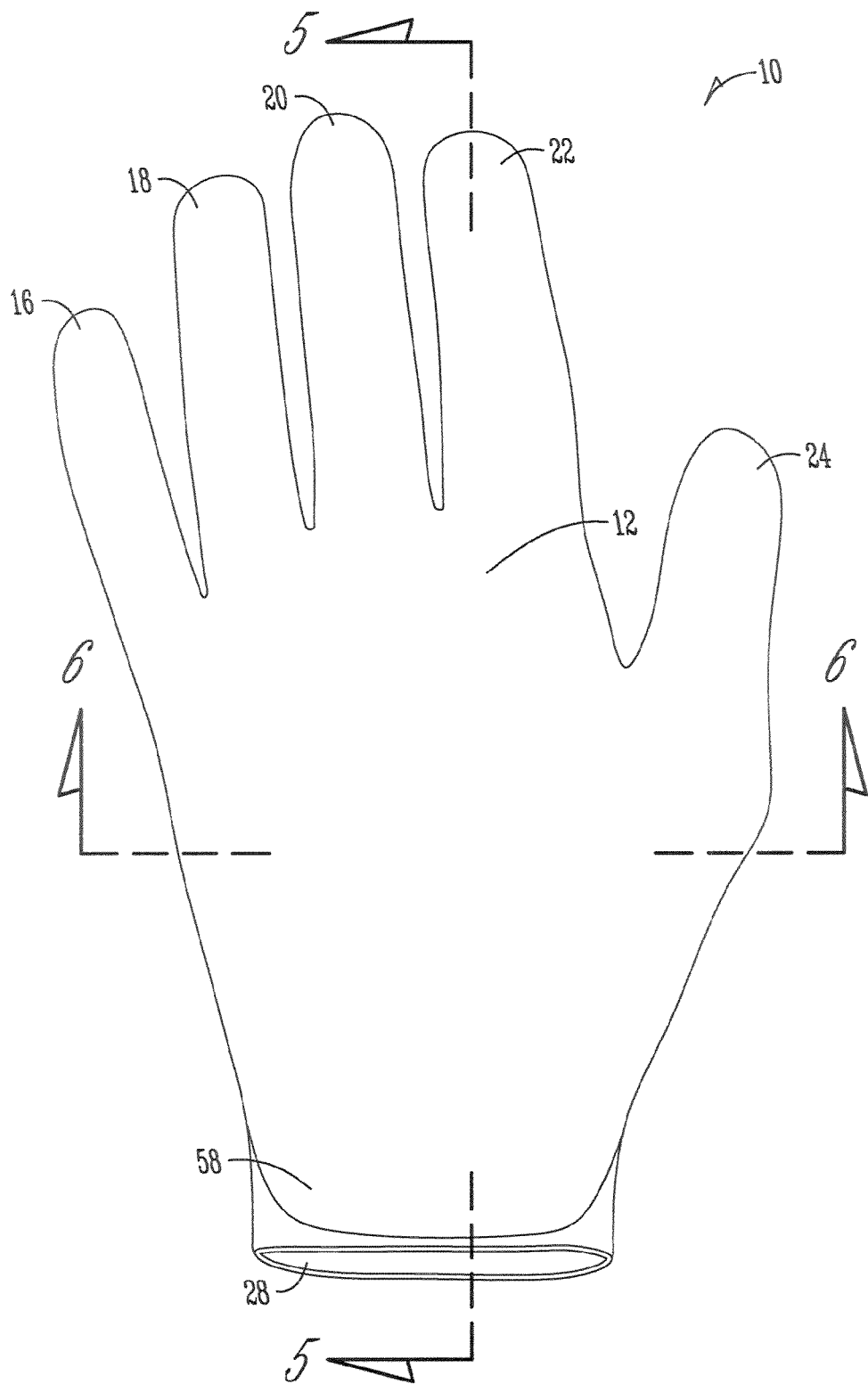
FIG. 1 is a top view of one of the gloves of the present invention.
Figure 2:
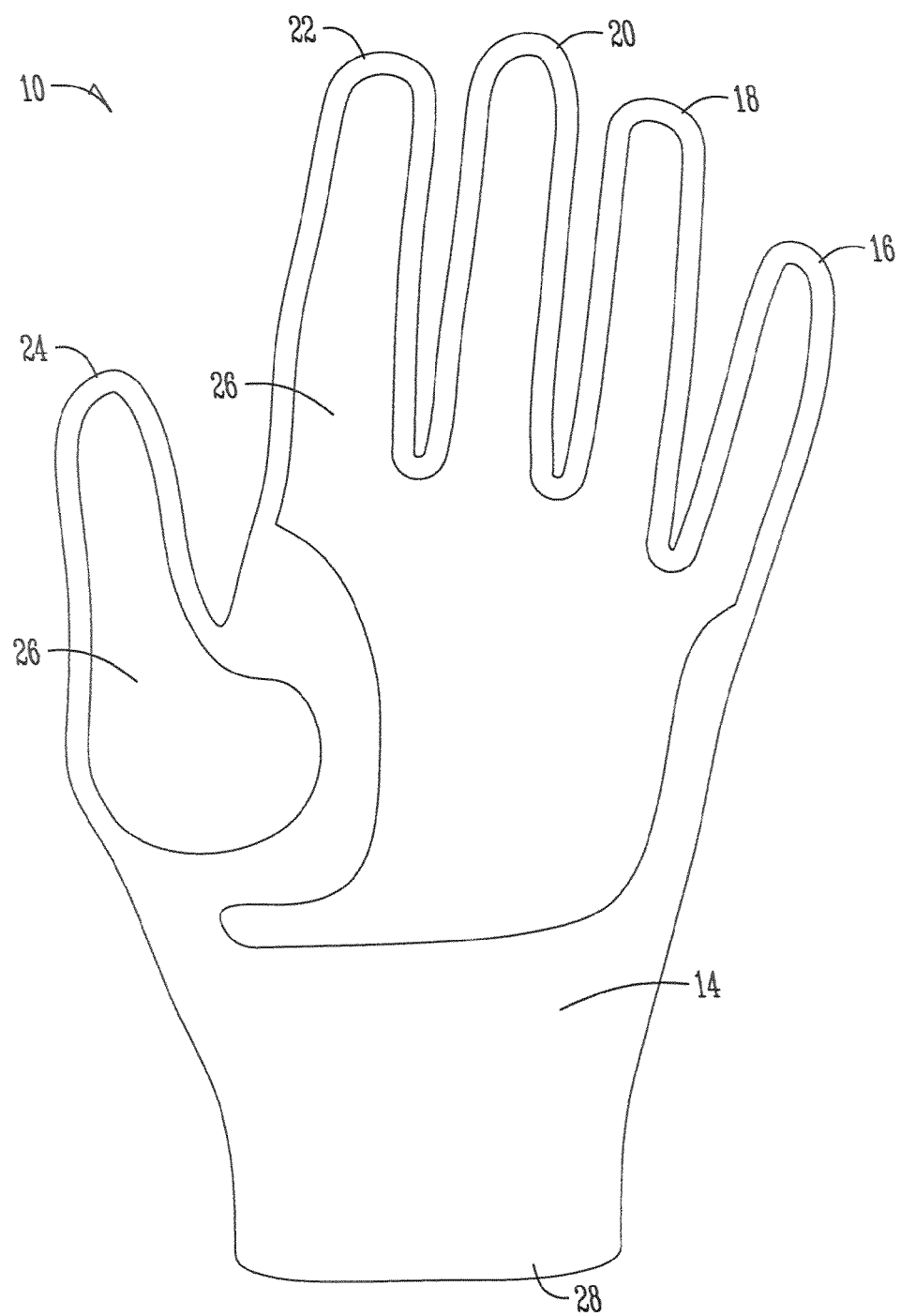
FIG. 2 is a palm view or a bottom view of one of the gloves of the present invention.

As can be seen in FIG. 2 the glove can have a palm or surface coating of silicon 26 which is optional. This palm or surface coating 26 enables a better grip on objects. It is often a helpful option with people having arthritic hands who have difficulty gripping tools and other objects. The glove 10 defines an interior cavity 28 in which a person may insert their hand.

Figure 3:
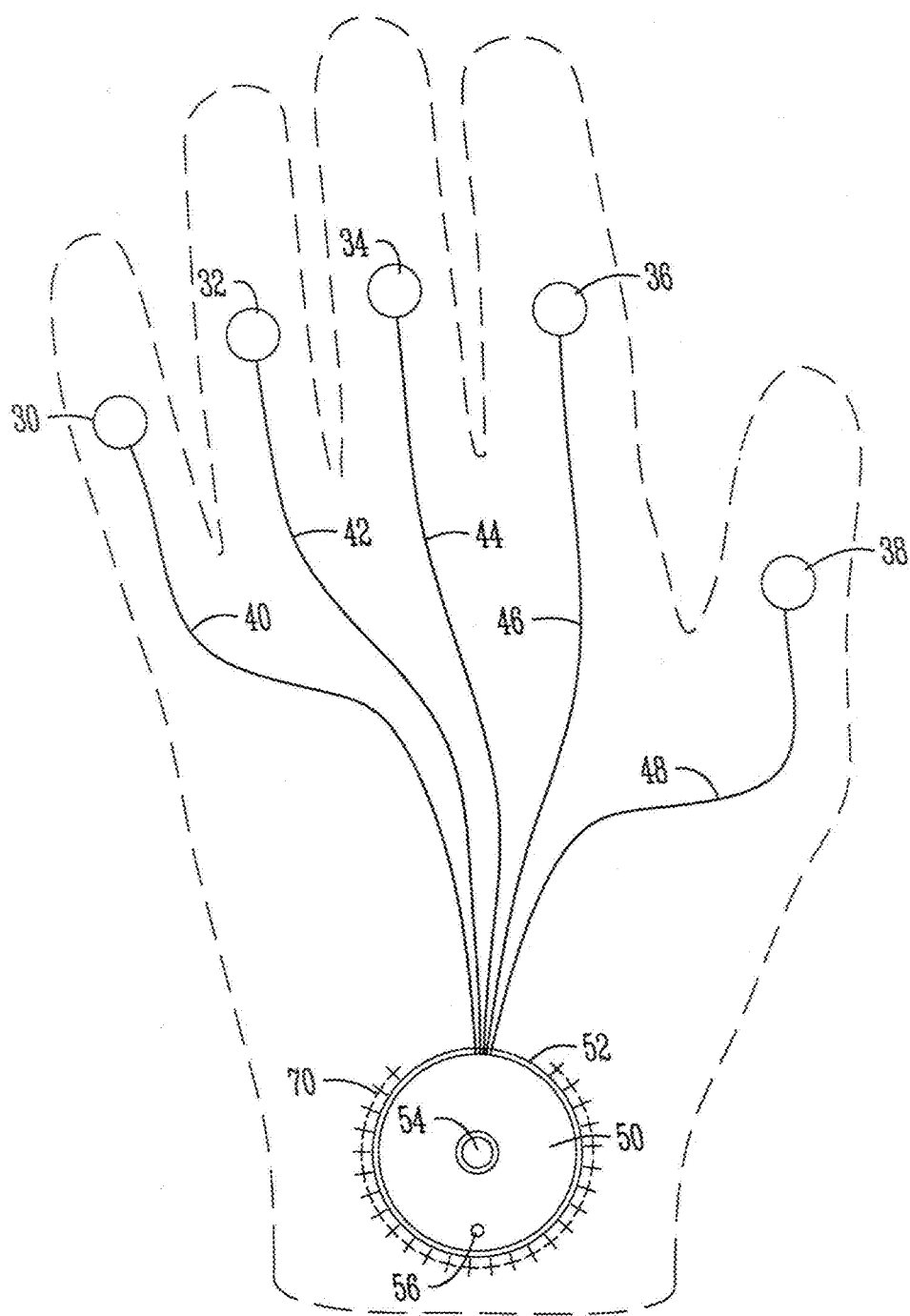
FIG. 3 is a schematic presentation of the electrical elements of the present invention as placed on top of the glove and under an overlay.
Figure 4:
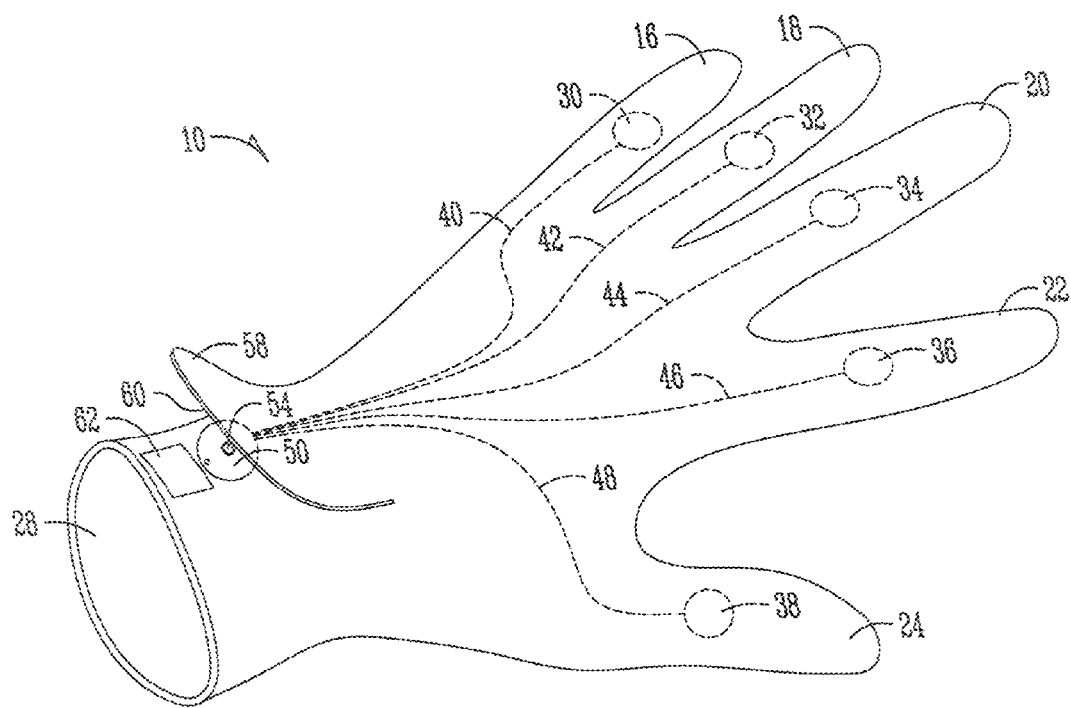
FIG. 4 is the glove in perspective view showing the overlay and how it may be laid back for access to the rechargeable battery.
Figure 5:
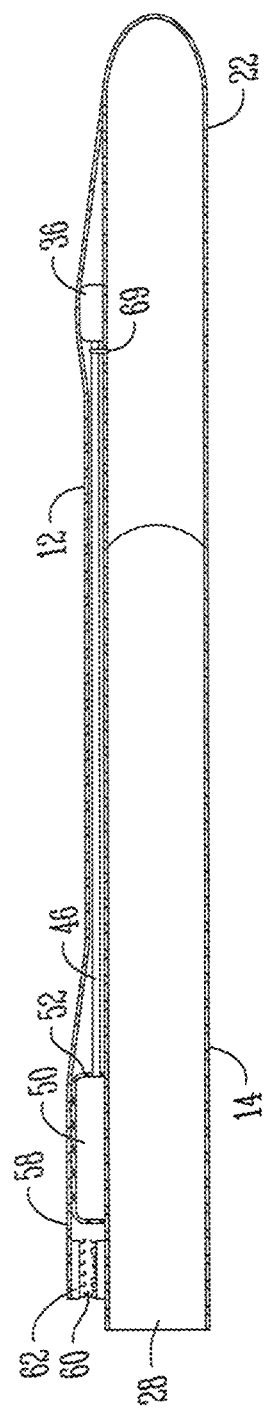
FIG. 5 is a sectional view along 5-5 of FIG. 1.
Figure 6:
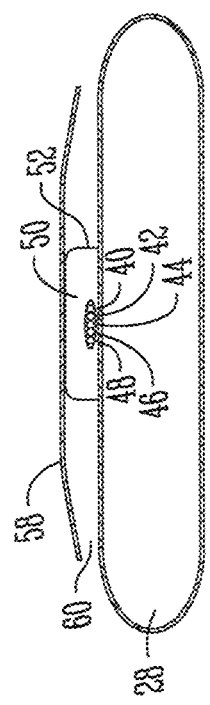
FIG. 6 is a sectional view along 6-6 of FIG. 1.

As best illustrated in FIG. 3 electrical vibrating massage is provided by five individual vibrating motors 30, 32, 34, 36 and 38 which are electrically connected by wires 40, 42, 44, 46 and 48 to power source such as battery 50. Battery 50 is inside of plastic housing 52 and carries an on/off switch 54 and has a charger plug in 56. The electrical assembly of FIG. 3 is placed in mating relationship on top of the glove illustrated in FIG. 1 and seamed over it as illustrated in FIG. 4 is an overlay 58 of the same stretchable fabric glove that is stitched to the top of the glove 10 of FIG. 1. The overlay 58 has a pocket 60 to be peeled back as illustrated in FIG. 4 to provide access to the battery 50 for recharging and for pushing the on/off switch 54. Pocket 60 may be hooked closed by a conventional hook and pile velcro fastening means, 62.

In operation the glove 10 is used in the following manner. A wearer inserts her hand in cavity 28, and instantly feels the compression over all parts of her hand. The individual vibrating motors 30, 32, 34, 36 and 38 are compressed against the upper forward side of the wearer's digits, generally forward of the most forward digit joint, which is often a location of arthritic pain. One motor is preferably located at the base of the thumb (CMC joint). The battery 50 is then in a position about the equivalent to the location of a watch, if worn by the user. On/off switch 54 is then turned on to activate the motors 30 to 38, and vibration therapy begins. Because of the compression, the vibration is felt well beyond the position of motors 30-38, namely carrying rearward in the fingers, and even to the palm of the wearer's hand. To stop the glove 10, pocket 60 may be opened and on/off button 54 is again pressed.

Because of the overlay 58, the glove 10 has an ordinary petite non-bulky glove appearance.

Certain constructional features are worthy of specific mention. The housing of the vibrating motors 30-38 is integral with the connecting lead wire. This is to prevent or minimize the fatigue associated with the thin wire in an active range of motion device in the hand. The glove with its stretchable fabric permits significant stretch, continuous orthotic compression and does not compromise memory integral nor does the stretching compromise the non-stretch wires that connect the switch and the motors. Straight stitch 69 holds the motor 30-38 in place and decreases migration of the motor within the structure of the glove itself as the glove is worn and used. Vibration induces migration so the straight stitch 69 technique holds the motor in place. The battery 50 also has a horseshoe stitch 70 which functions to keep this housing from migration. This is important otherwise the on/off switch 52 would move within the structural glove 10. Battery 50 can have a silicone cover to help reduce migration. The silicone fabric 26 is optional but many like it because it helps grip items.

Importantly the compression glove stretchable material helps communicate the vibration all around the hand. Gloves can be purchased in small, medium or large size. Compression of glove 10 helps retain the value of the massage for a longer period of time.

If desired a Piezo electric vibration generator may be used to replace the motors.

Motors 30-38 and battery 50 are available variety of sources. An example, one suitable supplier is Shenzhen Jingkefa Electronics Co. Limited. Batteries suitable for the vibrating motors 30-38 is a 3.7 volt lithium ion battery, which is rechargeable.

The gloves may be used and are especially adapted for arthritis, hand fatigue, tired aching joints and muscles, cold hands, and poor circulation.

What is claimed is:

1. An electro-massaging, orthotic compression glove, comprising;
   a stretchable fabric compression glove having upper and lower glove surfaces, glove fingers and a glove thumb which are all capable of compressing a wearer's hand and which defines an inner glove cavity;
   an electro-massage element mounted on said compression gloves upper surface above the inner glove cavity to provide vibration directly to a top side of a wearer's hand and digit joints; and
   an upper surface overlay of the same stretchable fabric as the stretchable fabric compression glove to cover the electro-massage element and provide a pocket for the electro massage element and still provide a normal glove appearance; and
   wherein the electro-massage element comprises a rechargeable power source electrically connected to motors associated with the upper surface of at least some of the glove fingers, and further wherein the rechargeable power source is held in place on the upper glove surface by a horseshoe-shaped stitching around a perimeter of the rechargeable power source that prevents migration of the rechargeable power source.

2. The glove of claim 1 wherein the overlay is at least partially releasably attached to the upper glove surface to provide at least partial access to the electro-massage element.

3. The glove of claim 1 wherein the electro-massage element is electrically connected to motors associated with the upper surface of each glove finger and thumb.

4. The glove of claim 1 wherein the stretchable fabric is about 90% cotton and about 10% spandex.

5. The glove of claim 1 wherein the stretchable fabric is about 92% cotton and about 8% spandex.

6. The glove of claim 3 which has an on-off switch associated with the rechargeable power source.

7. The glove of claim 1 which includes a palm surface coating on the exterior of the lower surface.

8. The glove of claim 5 wherein the rechargeable power source and on-off switch are housed in a single unit.

9. The glove of claim 1 wherein the motors are replaced with piezoelectric vibration generators.

10. The glove of claim 3 wherein the one of said motors associated with the thumb of said glove is positioned so as to be at a base of a wearer's thumb to stimulate CMC joint.

11. The glove of claim 1, wherein the motors are held in place on the upper glove surface in alignment with wearer's digit joints by straight stitching that decreases migration of the motors.

12. The glove of claim 8, wherein the on-off switch is facing an inner surface of the upper surface overlay.

* * * * *